United States Patent [19]

Buechler

[11] Patent Number: 5,233,042

[45] Date of Patent: Aug. 3, 1993

[54] COCAINE DERIVATIVES

[75] Inventor: Kenneth F. Buechler, San Diego, Calif.

[73] Assignee: Biosite Diagnostics, Inc., San Diego, Calif.

[21] Appl. No.: 808,515

[22] Filed: Dec. 16, 1991

[51] Int. Cl.$^5$ .................. C07D 451/06; C07D 451/10
[52] U.S. Cl. .................... 546/129; 546/130; 546/131
[58] Field of Search ............. 546/129, 130, 131

[56] References Cited

U.S. PATENT DOCUMENTS

| 3,888,866 | 6/1975 | Leute et al. | 546/130 |
| 4,102,979 | 7/1978 | Christenson | 546/131 X |
| 4,123,431 | 10/1978 | Soffer et al. | 546/131 X |

OTHER PUBLICATIONS

Ambre, John J., et al., A Kinetic Model of Benzolecgonine Disposition After Cocaine Administration in Humans, J. Anal. Tox. 15:17–20 (1991).

DeJong, A. W. K., Some Properties of the Ecgonines and Their Esters, Rec. Trav. Chim. 66:544–548 (1947).

Smith, R. Martin, Ethyl Esters of Arylhydroxy- and Arylhydroxymethoxycococaines in the Urines of Simultaneous Cocaine and Ethanol Users, J. Anal. Tox. 8:38–42 (1984).

Rafla, Fathi K. and Epstein, Robert L., Identification of Cocaine and its Metabolites in Human Urine in the Presence of Ethyl Alcohol, J. Anal. Tox. 3:59–63 (1979).

Primary Examiner—Richard L. Raymond
Attorney, Agent, or Firm—Lyon & Lyon

[57] ABSTRACT

Compounds are provided for the preparation of reagents, including labels which can be used in immunoassays of cocaine and cocaine metabolites. The compounds are derivatives of cocaine which are conjugated to antigenic proteins or polypeptides for the formation of antibodies for use in immunoassays. The compounds also may be conjugated to labels for use in immunoassays.

3 Claims, No Drawings

COCAINE DERIVATIVES

BACKGROUND OF THE INVENTION

Cocaine has been an abused drug for centuries. The ability to measure cocaine and cocaine metabolites, therefore, is vital to many medical and clinical ends, including the treatment of cocaine addiction.

Cocaine is rapidly metabolized in the body to primarily benzoylecgonine and ecgonine. In cases where alcohol (ethanol) consumption is also associated with cocaine use, the cocaine is also metabolized to benzoylecgonine ethyl ester and related aryl hydroxy metabolites (see, e.g., J. Anal. Toxicol. 8:38–42 (1984) and J. Anal. Toxicol. 3:59–63 (1979)). The benzoylecgonine ethyl ester and related metabolites have been identified to be more potent than cocaine and related metabolites and are believed to be responsible for deaths associated with simultaneous alcohol and cocaine use. Accordingly, there is a medical need for antibodies and diagnostics to rapidly detect benzoylecgonine ethyl ester and related metabolites.

The preparation of antibodies to cocaine and cocaine metabolites requires that a cocaine derivative be synthesized so that attachment to an antigenic polypeptide or protein is possible. In addition, the cocaine derivative is attached to various polypeptides, proteins or labels for use in screening antibodies and in the immunoassay process. The cocaine derivative should mimic the structure of the cocaine metabolite sought to be measured. Therefore, the selection and synthesis of the types of cocaine derivatives for attachment to proteins, polypeptides or labels is critical. In addition, the cocaine derivatives need to be stable to hydrolysis which might occur in an aqueous solution.

SUMMARY OF THE INVENTION

The present invention is directed to novel cocaine derivatives which are synthesized for attachment to antigens (proteins or polypeptides) for the preparation of antibodies to cocaine and cocaine metabolites. The resulting novel antigens may be used for the production of antibodies using standard methods. Once generated, the antibodies and the novel derivatives may be used in the immunoassay process.

DEFINITIONS

As used in the specification and claims, "receptor" shall mean a protein or polypeptide molecule capable of binding a ligand, typically an antibody. "Ligand" shall mean the binding partner to the receptor. "Label" shall mean the ligand derivative covalently coupled to a dye or a means capable of generating a signal in an immunoassay process. As used in the specification and claims, the following use of a parenthesis with a substituted benzene ring

shall indicate that the substitution following the benzene ring may be at any of the following ortho, meta or para positions.

DETAILED DESCRIPTION OF THE PREFERRED EMBODIMENTS

Novel compounds are described which are used in the generation of antibodies and, in the immunoassay process generally. The compounds are derivatives of cocaine and cocaine metabolites, primarily derivatives of benzoylecgonine. The benzoyl moiety of benzoylecgonine ultimately is modified to provide a chemical arm for attachment to proteins or polypeptides. The design of the synthesis of the chemical arm is constructed such that the benzoylecgonine derivative is displaced from the protein or polypeptide domain or label to allow the derivative to present itself to the binding domain of receptors.

In general, the compounds of this invention have the following formula:

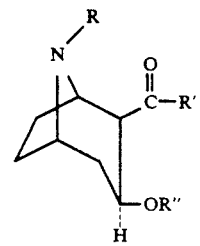

wherein:
R = —H, —CH$_3$
R' = —OH, —OCH$_3$, —OCH$_2$CH$_3$, —NHCH$_3$, —NHCH$_2$CH$_3$, —SCH$_3$, —SCH$_2$CH$_3$
R'' =

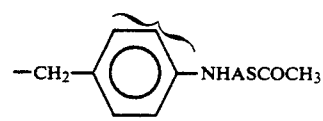

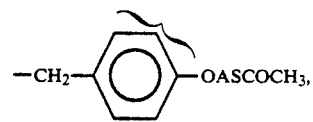

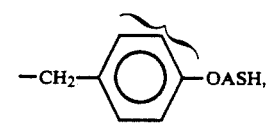

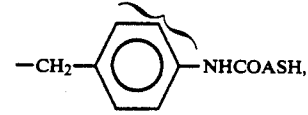

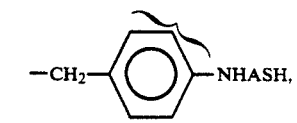

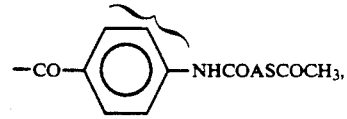

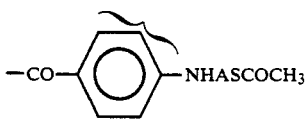

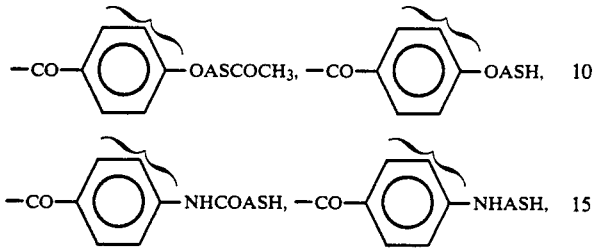

where A is an aliphatic linking group of from 1–10 carbons and 0–5 heteroatoms (chalcogen and nitrogen) and may be branched or straight chained.

In addition, the general form of protein or polypeptide molecules or labels derivatized with the cocaine derivatives are:

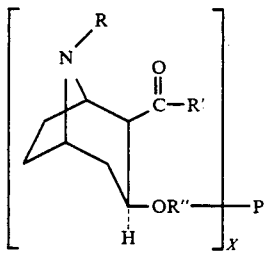

wherein:
R = —H, —CH3
R' = —OH, —OCH3, —OCH2CH3, —NHCH3, —NHCH2CH3, —SCH3, —SCH2CH3 .
R" =

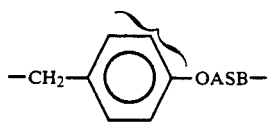

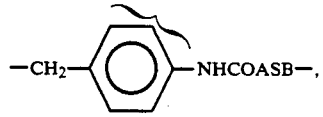

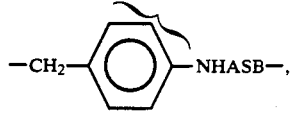

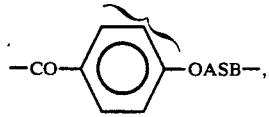

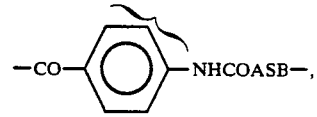

where A is an aliphatic linking group of from 1–10 carbons and 0–5 heteroatoms (chalcogen and nitrogen) and may be branched or straight chained; and where B is either of the following:

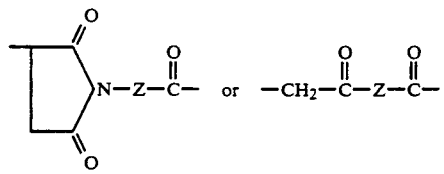

where Z is an aliphatic linking group of from 1–30 carbons and 10 heterocarbons and may be branched or straight chained; and where P = an antigenic protein or polypeptide or a protein, polypeptide or a label; and where x = at least one and not greater than 100.

Preferred compounds of this invention will have the following formula:

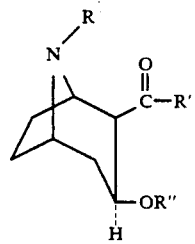

wherein:
= —H, —CH3
R' = —OH, —OCH3, —OCH2CH3, —NHCH3, —NHCH2CH3,
R" =

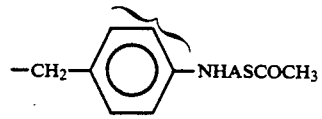

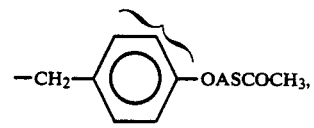

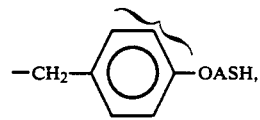

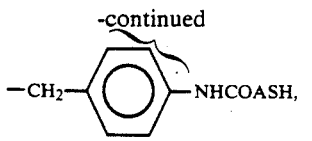

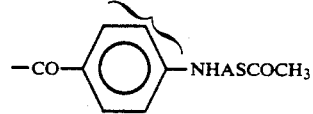

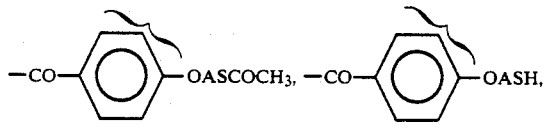

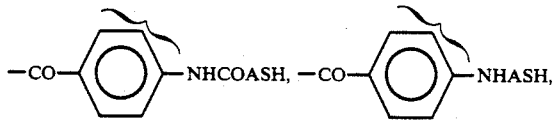

where A is an aliphatic linking group of from 1-10 carbons and 0-5 heteroatoms (chalcogen and nitrogen) and may be branched or straight chained.

In addition, the general form of the preferred protein or polypeptide molecules or labels derivatized with the cocaine derivatives are:

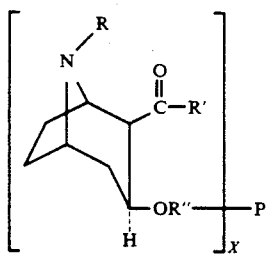

wherein:
R=—H, —CH3
R'=—OH, —OCH3, —OCH2CH3, —NHCH3, —NHCH2CH3, —SCH3, —SCH2CH3
R''=

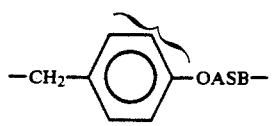

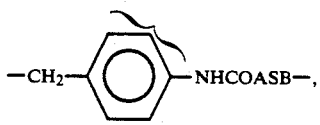

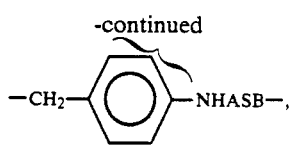

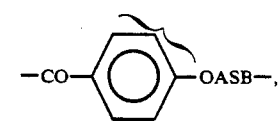

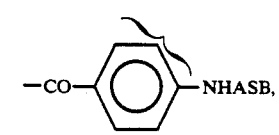

where A is an aliphatic linking group of from 1-5 carbons and 0-3 heteroatoms (chalcogen and nitrogen) and may be branched or straight chained; and
where B is either one of the following:

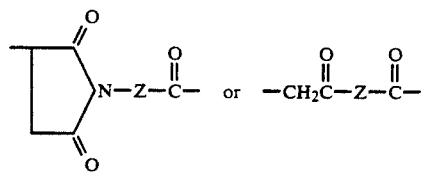

where Z is an aliphatic linking group of from 1-15 carbons and 0-5 heterocarbons and may be branched or straight chained; and
where P=an antigenic protein or polypeptide or a protein, polypeptide or label; and where x=at least 1 and not greater than 50.

Particularly preferred (best mode) compounds of this invention have the following formula:

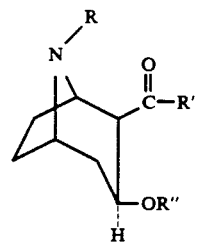

wherein:
R=—CH3
R'=—OH, —NHCH2CH3,
R''=

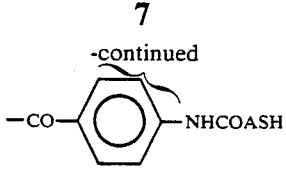

where A is an aliphatic linking group of from 1-5 carbons and 0-3 heteroatoms (chalcogen and nitrogen) and may be branched or straight chained.

In addition, the general form of particularly preferred (best mode) protein or polypeptide molecules or labels derivatized with the cocaine derivatives are:

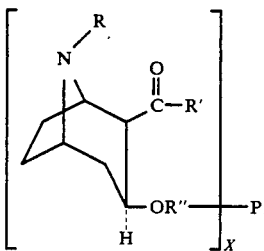

wherein:
R = —CH$_3$
R' = —OH, —NHCH$_2$CH$_3$,
R'' =

where A is an aliphatic linking group of from 1-5 carbons and 0-3 heteroatoms (chalcogen and nitrogen) and may be branched or straight chained; and where B is either of the following:

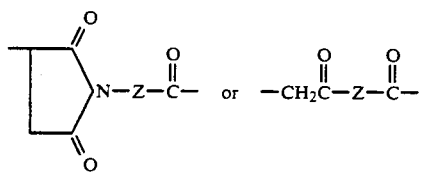

where Z is an aliphatic linking group of from 1-10 carbons and 0-5 heterocarbons and may be branched or straight chained; and where P = an antigenic protein or polypeptide or a protein, polypeptide or label; and where x = at least 1 and not greater than 30.

Of particular interest are compounds where the methyl ester of cocaine is changed to the methyl amide or the ethyl amide of benzoylecgonine. These compounds are preferred because they are less susceptible to hydrolysis in aqueous solutions than their ester analogues. Thus, the amide derivatives which mimic the configuration of the ester analogues can be used to prepare reagents for the preparation and screening of antibodies and for the immunoassay procedure. In addition to the amide moiety, the benzyl ether moiety which replaces the benzoyl ester also is less susceptible to hydrolysis in aqueous solutions. Thus, for example, the ethyl amide benzoyl ecgonine derivative is synthesized to prepare reagents for antibody preparation and screening and immunoassay for benzoylecgonine ethyl ester because the ethyl amide benzoylecgonine moiety mimics the configuration and is less susceptible to hydrolysis than the benzoylecgonine ethyl ester. In addition, it is believed that the methyl ester of cocaine is spontaneously hydrolyzed in the blood of man and animals. In the event that a highly specific antibody for cocaine (benzoylecgonine methyl ester) is required then immunizing with an antigenic cocaine conjugate may not be successful because the methyl ester of the cocaine derivative would have a very short half life in the blood and thus antibodies would actually be raised to the analogous benzoylecgonine derivative. This problem is overcome in the present invention by the novel derivatives described herein; that is, the methyl amide benzoylecgonine derivative is used to mimic the cocaine molecule. The methyl amide moiety is much less susceptible to hydrolysis than the methyl ester which assures greater success in the development of highly specific antibodies to cocaine.

EXPERIMENTAL EXAMPLES

Example 1

Synthesis of Acetylthiopropionic Acid

To a stirred solution of 3-mercaptopropionic acid (7 ml, 0.08 moles) and imidazole (5.4 g, 0.08 moles) in tetrahydrofuran (THF, 700 ml) was added dropwise over 15 minutes, under argon, a solution of 1-acetyl imidazole (9.6 g, 0.087 moles) in THF (100 ml). The solution was allowed to stir a further 3 hours at room temperature after which time the THF was removed in vacuo. The residue was treated with ice-cold water (18 ml) and the resulting solution acidified with ice-cold concentrated HCl (14.5 ml) to pH 1.5-2. The mixture was extracted with water (2×50 ml), dried over magnesium sulfate and evaporated. The residual crude yellow oily solid product (10.5 g) was recrystallized from chloroform-hexane to afford 4.8 g (41% yield) acetylthiopropionic acid as a white solid with a melting point of 44-45 C.

Example 2

Synthesis of p-Acetylthiopropionamide Benzoic Acid

Acetylthiopropionic acid (0.5 g, 0.0034 moles) was dissolved in anhydrous THF (3 ml). Carbonyldiimidazole (0.55 g, 0.0034 moles) was added and the mixture was stirred at room temperature for 45 minutes. A solution of p-aminobenzoic acid (0.46 g, 0.0034 moles) in anhydrous THF (2 ml) was added dropwise to the activated imidazolide while stirring and the reaction mixture was stirred for 2.5 hours at room temperature. The solvent was removed in vacuo and THF/water (7:4 ratio, 11 ml) was added to the residue to form a milky solution. The solution was warmed on a 50 C water bath, water (300 ml) was added, and the mixture was stored at 4 C overnight. The crystals were filtered and washed extensively with water and the product was dried in a vacuum desiccator. The recovered product (1.3 g) exhibited a melting point of 222-224 C.

Example 3

Synthesis of p-Acetylthiopropionamide Benzoylecgonine

To a stirred solution of p-acetylthiopropionamide benzoic acid (1.32 g, 0.0049 moles) in dry dimethylformamide (DMF, 8 ml) was added in one portion, under argon, carbonyldiimidazole (0.8 g, 0.0049 moles). The resulting solution was stirred at room temperature for 45 minutes and added in one portion, under argon, to a stirred solution of ecgonine hydrate (1.0 g, 0.0049 moles) in dry DMF (34 ml) containing 21% sodium ethoxide in ethanol (183 ul, 0.0049 moles). The solution was heated at 60-65 C for 6 hours after which time the DMF was removed in vacuo. The residual oil was subjected to chromatography on a 5×25 cm VYDAC RP C18 column using a linear gradient of 30 mM potassium phosphate, pH 4.6, to methanol to afford 0.53 g (19% yield) of p-acetylthiopropionamide benzoylecgonine phosphate salt as a colorless foam.

Example 4

Synthesis of p-Acetylthiopropionamide Benzoylecqonine Ethylamide

To a solution of p-acetylthiopropionamide benzoylecgonine (0.3 g, 0.00064 mol) and ethylamine hydrochloride (0.06 g, 0.0007 mol) in 2.9 ml dry dimethylformamide and pyridine (0.22 ml, 0.0027 mol) was added 1-ethyl-3-(3-dimethylaminopropyl)-carbodiimide hydrochloride (0.134 g, 0.0007 mol). The flask was sealed and allowed to sit at room temperature for 4 hr. Solvents were removed in vacuo and triturated with ethylether. The residue was dried in vacuo and the product was purified by high performance liquid chromatography. The residue was dissolved in 0.75 ml 0.5 M potassium phosphate, 0.1 M potassium borate buffer, pH 7. Crude product in the amount of 0.25 ml was injected onto a column (Vydac C18, 100 A pore size, 10μm particle size, 1×25 cm) and equilibrated in 0.02 M potassium phosphate, pH 4.6 at a flow rate of 2.0 ml/min. The product was eluted between 32 and 37 min with a gradient reaching 100% methanol in 50 min. The product of fractions from 4 chromatography runs was combined and solvents were removed in vacuo. The residue was triturated with methanol and filter. The methanol was removed in vacuo and 88 mg of p-acetylthiopropionamide benzoylecgonine ethylamide was recovered.

Preparation of Benzoylecqonine Analoque Attached to Keyhole Limpet Hemocyanin (KLH), Bovine Serum Albumin (BSA), and Alkaline Phosphatase (AP)

The attachment of benzoylecgonine analogue to proteins is achieved by reacting the free thiol, generated by hydrolysis of the p-acetylthiopropionamide benzoylecgonine, to proteins which contain a reactive maleimide that is the result of derivatization of the protein with succinimidyl 4-(N-maleimidomethyl)cyclohexane-1-carboxylate (SMCC, Pierce Chemical Co.). The free thiol form of the benzoylecgonine ligand analogue was generated by dissolving 30 mg of p-acetylthiopropionamide benzoylecgonine phosphate salt in 2.6 ml of 0.12 M potassium carbonate in 80% methanol and at 3 minutes into the reaction the thiol concentration was measured by DTNB to be 18.9mM. Potassium phosphate, potassium borate (0.5M/0.1 M), pH 7 was added to the thiol solution and the pH was adjusted to 7 with 1N hydrochloric acid. The thiol concentration was determined by the method of Ellman (Ellman, G. L., *Arch. Biochem. Biophys.*, 82, 70 (1959)) to be 15 mM. The pH of the solution was adjusted to 7.0 with glacial acetic acid prior to coupling to proteins.

KLH (6 ml of 14mg/ml) was reacted with sulfosuccinimidyl 4-(N-maleimidomethyl)cyclohexane-1-carboxylate (SULFO-SMCC by adding 15 mg of SULFO-SMCC and maintaining the pH between 7 and 7.5 with 1N potassium hydroxide over a period of one hour at room temperature while stirring. The protein was separated from the unreacted SULFO-SMCC by gel filtration chromatography in 0.1 M potassium phosphate, 0.02 M potassium borate, and 0.15 M sodium chloride, pH 7.0, and 24 ml of KLH-maleimide was collected at a concentration of 3.1 mg/ml. The free thiol containing benzoylecgonine analogue (1.7 ml of 14 mM) was added to 6 ml of 3.1 mg/ml KLH-maleimide and the solution was stirred for 4 hours at 4 C and then dialyzed against 3 volumes of one liter each of pyrogen-free phosphate-buffered saline, pH 7.4, prior to immunization.

BSA (3.5 ml of 20 mg/ml) was reacted with SMCC by adding a solution of 6.7 mg of SMCC in 0.3 ml acetonitrile and stirring the solution for one hour at room temperature while maintaining the pH between 7 and 7.5 with 1N potassium hydroxide. The protein was separated from unreacted materials by gel filtration chromatography in 0.1 M potassium phosphate, 0.02 M potassium borate, 0.15 M sodium chloride, pH 7.0. The free thiol form of the benzoylecgonine ligand analogue (0.17 ml of 14 mM) was added to the BSA-maleimide (2 ml at 8.2 mg/ml) and the solution was stirred for 4 hours at 4 C. The solution was used to coat microtiter plates for the detection of antibodies that bind the benzoylecgonine ligand analogue by standard techniques.

AP (1.5 ml of 10.9 mg/ml) was reacted with SULFO-SMCC by adding 3.1 mg of SULFO-SMCC to the solution and stirring at room temperature for one hour while maintaining the pH between 7.0 and 7.5 using 1 M potassium hydroxide. The protein was separated from the unreacted materials by gel filtration chromatography in 0.1 M potassium phosphate, 0.02 M potassium borate, 0.15 M sodium chloride, pH 7.0. The free thiol form of the benzoylecgonine ligand analogue (0.02 ml of 12 mM) was added to the AP-maleimide (0.2 ml at 3.56 mg/ml) and the solution was stirred for 1.5 hours at 4 C. The protein was separated from unreacted materials by gel filtration chromatography in 0.1 M potassium phosphate, 0.02 M potassium borate, 0.15 M sodium chloride, pH 7.0, and the benzoylecgonine ligand analogue conjugate was diluted for use in assays.

Preparation of Benzoylecgonine Ethylamide Analogue Attached to Ferritin, Bovine Serum Albumin (BSA), and Alkaline Phosphatase (AP)

The attachment of benzoylecgonine ethylamide analogue to proteins is achieved by reacting the free thiol, generated by hydrolysis of the p-acetylthiopropionamide benzoylecgonine ethylamide, to proteins which contain a reactive maleimide that is the result of derivatization of the protein with succinimidyl 4-(N-maleimidomethyl)cyclohexane-1-carboxylate (SMCC, Pierce Chemical Co.). The free thiol form of the benzoylecgonine ligand analogue was generated by dissolving 8 mg of p-acetylthiopropionamide benzoylecgonine ethylamide phosphate salt in 0.71 ml of 0.12 M potassium carbonate in 80% methanol and at 3 min into the reaction the thiol concentration was measured by DTNB to be 19.5 mM. Add 0.25 ml 0.5 M potassium phosphate/0.1 M potassium borate, pH 7, to the thiol solution and adjust the pH to 7 with 1 N hydrochloric acid. The thiol concentration was then 12.7 mM.

Ferritin (Horse spleen, Sigma Chemical Co.), (3 ml of 10 mg/ml) was reacted with sulfosuccinimidyl 4-(N-maleimidomethyl)cyclohexane-1-carboxylate (SULFO-SMCC) by adding 15 mg of SULFO-SMCC and maintaining the pH between 7 and 7.5 with 1N potassium hydroxide over a period of one hour at room temperature while stirring. The protein was separated from the unreacted SULFO-SMCC by gel filtration chromatography in 0.1 M potassium phosphate, 0.02 M potassium borate, and 0.15 M sodium chloride, pH 7.0, and 9 ml of ferritin-maleimide was collected at a concentration of 3.1 mg/ml. The free thiol containing benzoylecgonine ethylamide analogue (0.3 ml of 12.7 mM) was added to the ferritin-maleimide and the solution was stirred for 4 hours at 4 C and then dialyzed against 3 volumes of one liter each of pyrogen-free phosphate-buffered saline, pH 7.4.

BSA (3.5 ml of 20 mg/ml) was reacted with SMCC by adding a solution of 6.7 mg of SMCC in 0.3 ml acetonitrile and stirring the solution for one hour at room temperature while maintaining the pH between 7 and 7.5 with 1N potassium hydroxide. The protein was separated from unreacted materials by gel filtration chromatography in 0.1 M potassium phosphate, 0.02 M potassium borate, 0.15 M sodium chloride, pH 7.0. The free thiol form of the benzoylecgonine ethylamide analogue (0.2 ml of 12.7 mM) was added to the BSA-maleimide (2 ml at 8.2 mg/ml) and the solution was stirred for 4 hours at 4 C. The solution was used to coat microtiter plates for the detection of antibodies that bind the benzoylecgonine ethylamide analogue by standard techniques.

AP (1.5 ml of 10.9 mg/ml) was reacted with SULFO-SMCC by adding 3.1 mg of SULFO-SMCC to the solution and stirring at room temperature for one hour while maintaining the pH between 7.0 and 7.5 using 1 M potassium hydroxide. The protein was separated from the unreacted materials by gel filtration chromatography in 0.1 M potassium phosphate, 0.02 M potassium borate, 0.15 M sodium chloride, pH 7.0. The free thiol form of the benzoylecgonine ethylamide analogue (0.02 ml of 12.7 mM) was added to the AP-maleimide (0.2 ml at 3.56 mg/ml) and the solution was stirred for 1.5 hours at 4 C. The protein was separated from unreacted materials by gel filtration chromatography in 0.1 M potassium phosphate, 0.02 M potassium borate, 0.15 M sodium chloride, pH 7.0, and the benzoylecgonine ethylamide analogue conjugate was diluted for use in assays.

Preparation Of Latex-Immobilized Affinity-Purified Goat IqG Antibody Against The Fc Fragment Of Mouse IqG Affinity-purified goat-anti-mouse Fc (BiosPacific) and polystyrene latex particles (sulfated, 1.07 μm) (Interfacial Dynamics) were incubated separately at 45 C for one hour, the antibody solution being buffered with 0.1 M 2-(N-morpholino) ethane sulfonic acid at pH 5.5. While vortexing the antibody solution, the suspension of latex particles was added to the antibody solution such that the final concentration of antibody was 0.3 mg/ml and the solution contained 1% latex solids. The suspension was incubated for 2 hours at 45 C prior to centrifugation of the suspension to pellet the latex particles. The latex pellet was resuspended in 1% bovine serum albumin in phosphate-buffered-saline (PBS) and incubated for one hour at room temperature. Following centrifugation to pellet the latex, the pellet was washed three times by resuspension in PBS and centrifugation. The final pellet was resuspended in borate-buffered-saline, 0.1% sodium azide, pH 8.0, at a latex concentration of 1% solids. A 1% suspension of this latex preparation was capable of binding 40 μg/ml of monocloal antibody.

Production and Primary Selection of Monoclonal Antibodies

Immunization of Balb/c mice was performed according to the method of Liu, D., Purssell, R., and Levy, J. G., Clin Chem, 25, 527–538 (1987). Fusions of spleen cells with SP2/0-Ag14 myeloma cells, propagation of hybridomas, and cloning were performed by standard techniques. Selection of hybridomas for further cloning began with culture supernatant at the 96-well stage. A standard ELISA procedure was performed with benzoylecgonine attached to BSA adsorbed to the ELISA plate. Typically, a single fusion was plated out in twenty plates and approximately 10–20 wells per plate were positive by the ELISA assay. At this stage, a secondary selection could be performed if antibodies to the SMCC part of the linking arm were to be eliminated from further consideration. An ELISA assay using BSA derivatized with SMCC but not containing the benzoylecgonine derivative identified which of the positive clones that bound the BSA-benzoylecgonine ligand analogue were actually binding the SMCC-BSA. Depending on the particular objectives for the antibodies obtained, the antibodies specific for SMCC-BSA may be eliminated at this step.

The foregoing examples describe the invention in detail by way of illustration and example. It will be obvious to those skilled in the art that changes and modifications may be practiced within the scope of the following claims.

I claim:

1. Compounds of the formula:

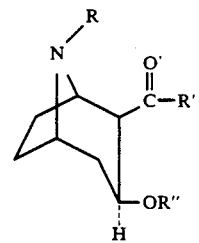

wherein:
R = —H, —CH₃
R' = —OH, —OCH₃, —OCH₂CH₃, —NHCH₃, —NHCH₂CH₃, —SCH₃, —SCH₂CH₃
R" =

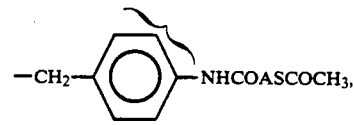

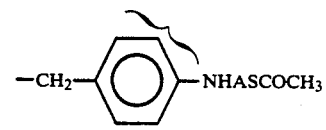

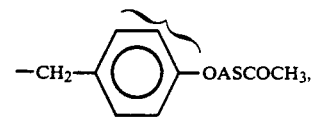

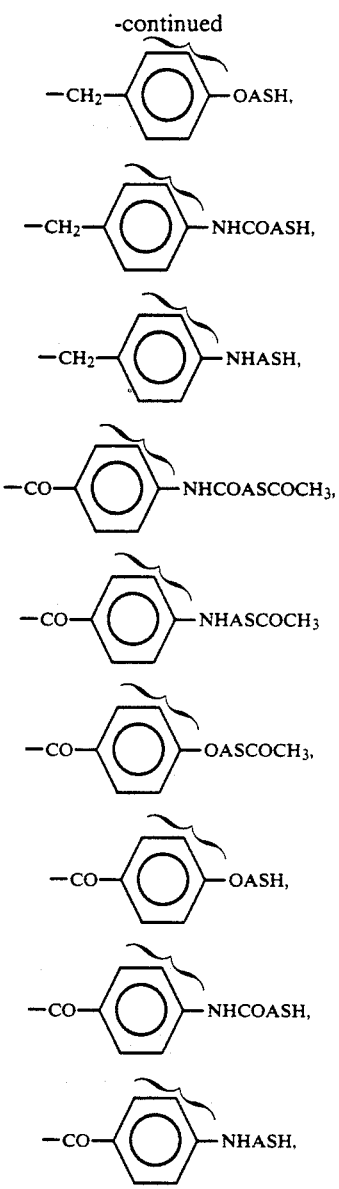

where A is an aliphatic linking group of from 1–10 carbons and 0–5 heteroatoms selected from chalcogen and nitrogen and may be branched or straight chained.

2. Compounds of the formula:

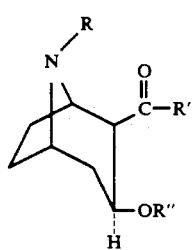

wherein:
R = —H, —CH₃
R' = —OH, —OCH₃, —OCH₂CH₃, —NHCH₃, —NHCH₂CH₃,
R'' =

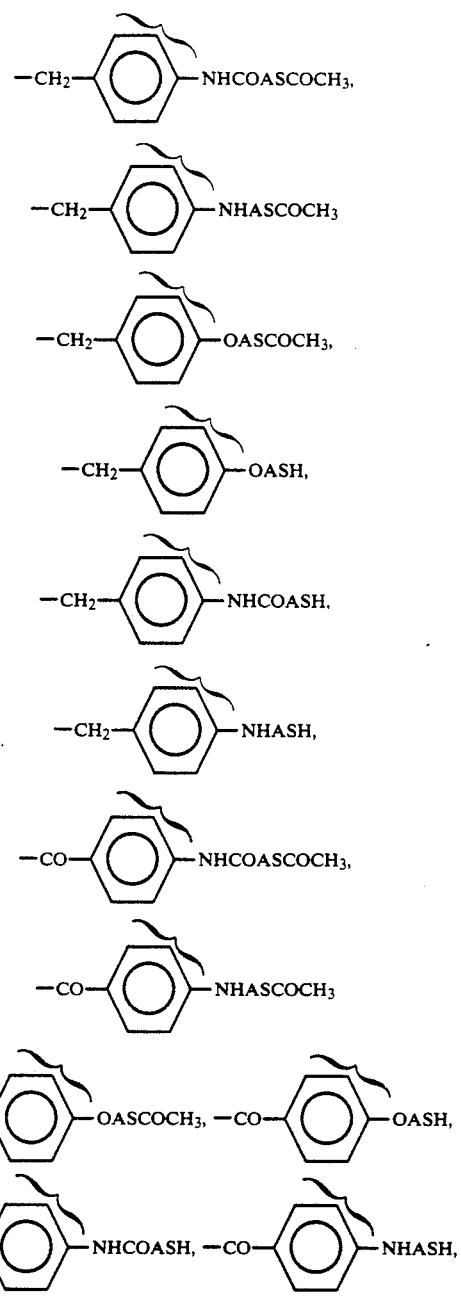

where A is an aliphatic linking group of from 1–10 carbons and 0–5 heteroatoms selected from chalcogen and nitrogen and may be branched or straight chained.

3. Compounds of the formula:

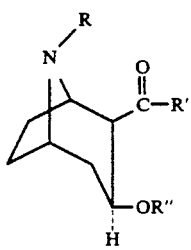

wherein:

R=—CH₃
R'=—OH, —NHCH₂CH₃,
R"=
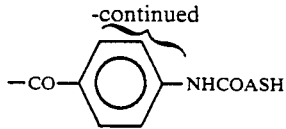
where A is an aliphatic linking group of from 1–5 carbons and 0–3 heteroatoms selected from chalcogen and nitrogen and may be branched or straight chained.
* * * * *